United States Patent
Faccioli et al.

(10) Patent No.: US 8,562,687 B2
(45) Date of Patent: Oct. 22, 2013

(54) MODULAR SPACER DEVICE FOR JOINTS OF THE HUMAN BODY

(75) Inventors: Giovanni Faccioli, Monzambano (IT); Renzo Soffiatti, Nogara (IT)

(73) Assignee: Tecres S.p.A., Sommacampagna (Verona) (IT)

( * ) Notice: Subject to any disclaimer, the term of this patent is extended or adjusted under 35 U.S.C. 154(b) by 48 days.

(21) Appl. No.: 13/236,154

(22) Filed: Sep. 19, 2011

(65) Prior Publication Data

US 2013/0073049 A1   Mar. 21, 2013

(51) Int. Cl.
*A61F 2/38* (2006.01)
(52) U.S. Cl.
USPC .............. 623/20.21; 623/20.32; 623/20.14; 623/20.15
(58) Field of Classification Search
CPC ........................................... A61F 2/38
USPC ................ 623/20.21–20.28, 20.14, 20.15, 623/20.32–20.34
See application file for complete search history.

(56) References Cited

U.S. PATENT DOCUMENTS

| | | | | |
|---|---|---|---|---|
| 3,924,277 A | * | 12/1975 | Freeman et al. | 623/20.21 |
| 2005/0246029 A1 | * | 11/2005 | Keller | 623/20.31 |
| 2008/0027557 A1 | * | 1/2008 | Tuke | 623/20.32 |
| 2009/0265013 A1 | * | 10/2009 | Mandell | 623/20.21 |
| 2009/0326667 A1 | * | 12/2009 | Williams et al. | 623/20.31 |
| 2011/0029090 A1 | * | 2/2011 | Zannis et al. | 623/20.28 |

FOREIGN PATENT DOCUMENTS

IT          1278853  B1    11/1997

* cited by examiner

*Primary Examiner* — Jason-Dennis Stewart
(74) *Attorney, Agent, or Firm* — Tutunjian & Bitetto, P.C.

(57) ABSTRACT

Disposable modular spacer device of the articulation of a knee including a tibial element, constrainable to an end of the tibial bone in proximity of the articulation of the knee and including a lower surface and an upper surface provided with a radius of curvature R2, and a femoral element, including an inner surface, constrainable to an end of the femoral bone at the articulation of the knee and an outer convex surface, provided with a radius of curvature R1 and in contact with the upper surface of the tibial element, the tibial element and the femoral element having various dimensions or sizes, the tibial element being configured so as to be coupled with any size of the femoral element to adapt the dimensions of the modular spacer device with the dimensions of the bone ends to which it should be connected.

25 Claims, 3 Drawing Sheets

MODULAR SPACER DEVICE FOR JOINTS OF THE HUMAN BODY

BACKGROUND

1. Technical Field

The present invention refers to a modular spacer device for the temporary replacement of articular prostheses that require to be removed for various reasons, for example due to an infection. Such modular spacer device allows, over the period of time required for treating the articulation, preserving the space required for the implantation of a new articular prosthesis and guaranteeing a good movement of the articulation.

2. Description of Related Art

In the field of implantology of articular prostheses it is known that such devices can be subjected to removal due to various reasons, in particular, due to local infections of the articulation after the implantation of the prosthesis.

In such cases, the infected prosthesis cannot be immediately replaced with a new prosthesis, given that the seat of the articulation is required to be treated using suitable antibiotic medicines.

During the period of time required for the antibiotic treatment it is fundamental to preserve an articular space required for the implantation of a new articular prosthesis and prevent the tissues from shortening, the articulation from being subjected to atrophy and the muscles from losing tonicity.

Such technique is known as "two-stage implantation" of the articular prostheses.

There are known temporary articular spacers of the knee, manually formed by a surgeon directly during the surgical intervention of implanting the spacer.

Such devices are made of the bone cement and suitably shaped, manually, in the instants preceding the implantation in the articular seat.

A drawback of such treatment method lies in the fact that the cement is formed and shaped directly during the intervention, actually increasing the duration of the operation and the difficulties for the surgeon.

Furthermore, given that in the formation of the bone cement potentially toxic harmful substances are used, it is advisable to reduce the time of contact of the surgeon or operator therewith to the maximum.

Furthermore, the manual forming of the spacer may determine the presence of faults that may reduce the mobility offered by the articulation obtained using a similar spacer.

Pre-formed articulation spacers to be implanted without requiring any type of forming during the intervention are also available in the market. However, such devices reveal the drawback of being made up of a femoral part and a tibial part combined to each other a priori; in other words they cannot be easily adapted to the anthropomorphic dimensions, even variable, of the patient.

A consequence of the erroneous adaptability of the known spacers to the anthropomorphic dimensions of the patient lies in the impossibility of guaranteeing a good mobility of the articulation and, thus, ensuring a good quality of life to the patient awaiting the implantation of a new articular prosthesis.

SUMMARY OF THE INVENTION

An object of the present invention is to improve the state of the prior art.

Another object of the present invention is to provide a spacer device for the articulation of the knee that is pre-formed and which is compatible with the various dimensions or sizes of the bone ends to which it is applied.

A further object of the present invention is to provide a spacer device for the articulation of the knee that is capable of allowing a high and stable movement of the articulation in question to ensure the patient a good quality of life during the period of rehabilitation following the implantation of the spacer, even in the presence of anatomic variations between the tibial bone and the femoral bone of a patient.

According to an aspect of the present invention there is provided a modular spacer device for the articulation of the knee.

The claims refer to preferred and advantageous embodiments of the invention.

BRIEF DESCRIPTION OF THE DRAWINGS

Further characteristics and advantages of the present invention will be more apparent from the detailed description of a preferred but not exclusive embodiment of a modular spacer device for a knee, illustrated by way of non-limiting example in the attached drawings wherein.

DETAILED DESCRIPTION OF PREFERRED EMBODIMENTS

Figure 1:
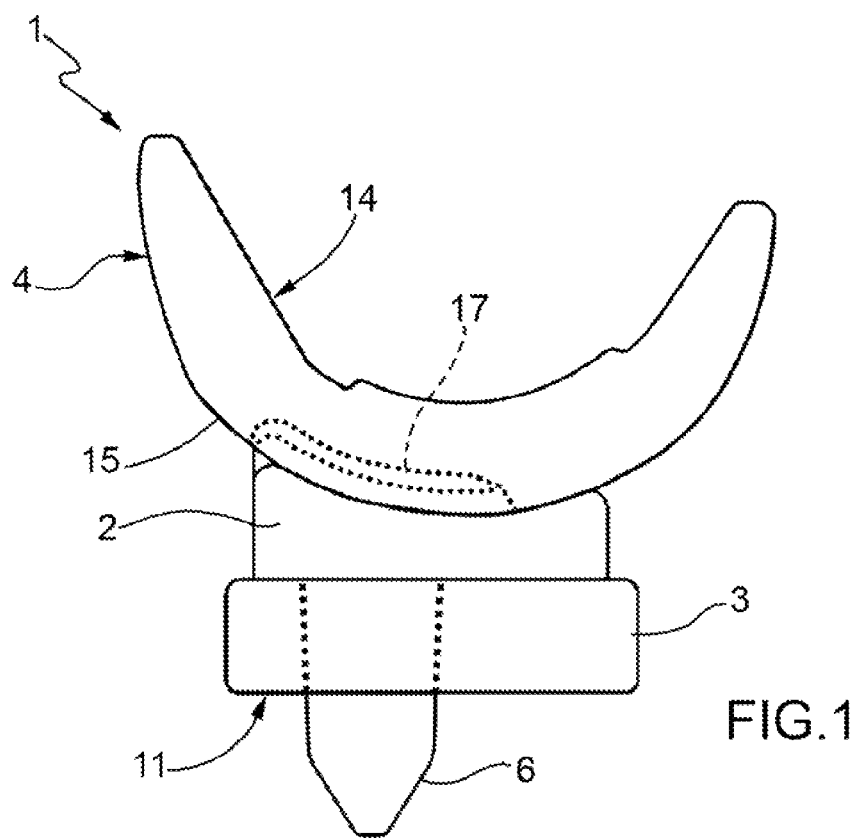
FIG. 1 is a lateral view of the spacer device according to the present invention.

With reference to the attached figures, a disposable temporary modular spacer device of the articulation of a knee is schematically indicated with 1.

For the sake of further clarity, such disposable temporary modular spacer device of the articulation of a knee will be indicated hereinafter as "modular spacer device".

Such modular spacer device 1 comprises a tibial element 2, adapted to be constrained to the end of the tibial bone in proximity of the articulation of the knee, and a femoral element 4 adapted, on one side, to be constrained to the end of the femoral bone at the articulation of the knee and, on the other side, to be in contact with the tibial element 2.

The modular spacer device 1 may further comprise a shim 3. The shim 3 is optional and can be used for increasing the height of the modular spacer device 1 to compensate possible absence or strong resection of the tibial bone of the patient and/or to extend the articulation, if required.

Furthermore, the shim 3 allows offering a large surface for arranging the tibial element 2, otherwise not available, in given extreme conditions, at the sectioned end of the tibial bone of the patient.

The shim 3 is positioned at the tibial part of the patient and, in particular, beneath the tibial element 2. Thus, though obtaining the functions listed above, the shim 3 does not interfere with the articulation provided by the tibial element 2 with the femoral element 4. Thus, both in the presence of the shim 3 and when it is absent, the articulation is always preserved.

The tibial 2 and femoral 4 elements and the shim 3 are preformed and entirely made of biologically compatible material.

Such biologically compatible material is porous and it can be selected from among metals, metal alloys, organo-metallic compounds, ceramics, plastic materials and/or a combination thereof.

Specifically, the aforementioned plastic materials can be selected from among thermoplastic polymers, such as acrylic resins, polyethylene, polypropylene, polyester, etcetera, thermoformable polymers, and other similar materials.

In a version of the present invention, the biologically compatible material is a bone cement, for example of the type described in the Italian patent No. 1278853, on behalf of the applicant, the disclosure of which is incorporated herein by reference.

The aforementioned biologically compatible material, due to the porosity thereof, may be pre-impregnated, by the producer of the modular spacer device 1, using pharmaceutical and therapeutic products.

In another embodiment, the biologically compatible material, originally without medicinal substances, may be added, possibly by impregnation, using pharmaceutical and therapeutic products during the surgical intervention, in the instants preceding implantation thereof.

Still, in another embodiment, the biologically compatible material pre-impregnated by the producer of the modular spacer device 1 using pharmaceutical and therapeutic products, may be further added, during the surgical intervention, in the instants preceding implantation thereof, using pharmaceutical and therapeutic products, identical or different from those already contained therein, depending on the surgery requirements.

The shim 3 is provided with a hole 8, which is through and positioned substantially at a central position with respect to the shim 3.

The tibial element 2 is provided with a lower surface 7, substantially flat, and an upper concave surface 16.

In a version of the invention, the tibial element 2, as indicated in FIG. 1, is provided with a substantially rod-like element 6, for example a pin or a stem, which extends, from the lower surface 7 of the tibial element 2, downwards substantially in longitudinal direction with respect to the tibial bone of the patient.

Such substantially rod-like element 6 is positioned at the hole 8 of the shim 3 and it has a diameter slightly smaller than that of the hole 8. Thus, the substantially rod-like element 6 is adapted to be inserted into and traverse the hole 8 obtained in the shim 3.

Thus, this allows a correct relative positioning between the tibial element 2 and the shim 3, in order to guarantee coaxiality.

The tibial element 2 can be directly constrained to the portion of the tibial bone of the patient or, if present, to the shim 3. Such constraint can be obtained by means of the bone cement.

The shim 3 has an upper surface 9 and a lower surface 11. Both surfaces 9 and 11 of the shim 3 are substantially flat.

The upper surface 9 of the shim 3 is provided with first ribs 10 and respective first recesses. Such first recesses correspond to the space comprised between two adjacent first ribs 10.

Figure 5:
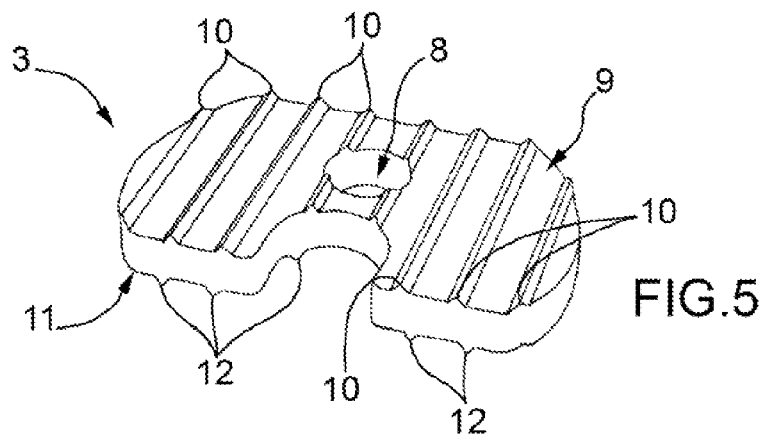
FIG. 5 is a perspective view of a further detail of the device according to FIG. 1.
Figure 8:
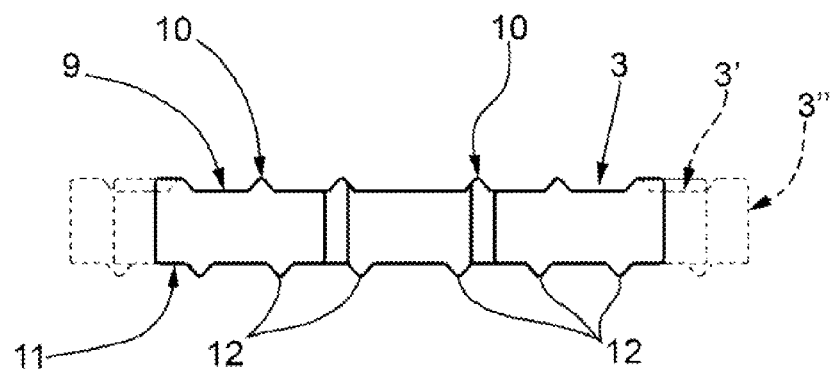
FIG. 8 is a front view of the various sizes of the detail according to FIG. 5.

In an embodiment, as indicated in FIGS. 5 and 8, such first ribs 10 extend linearly along the upper surface 9 of the shim 3, and they are suitably spaced from each other.

In a further version of the invention, the first ribs 10 may also develop differently, for example webbed, or having any other configuration, without departing from the scope of protection of the present invention.

The presence of such first ribs 10 and respective first recesses allows holding the bone cement, thus preventing the latter from being dispersed during the possible stage of joining the tibial element 2 with the shim 3.

The lower surface 11 of the shim 3 is provided with second ribs 12 and respective second recesses, similar to the first ribs 10 and to the first recesses described previously regarding the upper surface 9.

Such second recesses correspond to the space comprised between two adjacent second ribs 12.

The shim 3 is adapted to be constrained to the end of the tibia using bone cement.

The second ribs 12, analogously to what was described previously regarding the first ribs 10 of the upper surface 9, allow holding within the respective second recesses the bone cement and prevent the latter from entirely flowing out during the stage of implanting the shim 3 on the tibia of the patient.

The lower surface 7 of the tibial element 2 has third ribs 22 and corresponding third recesses, similar to the first ribs 10 of the upper surface 9 and to the second ribs 12 of the lower surface 11 of the shim 3.

The third recesses have the same characteristics described previously regarding the first recesses and regarding the second recesses. In the version in which the shim 3 is not used, the surface 7 of the tibial element 2 is arranged in contact with the tibial bone of the patient. Also in this case, the third ribs 22 and the relative third recesses prevent the bone cement from entirely flowing out during the stage of implanting the tibial element 2 on the tibia of the patient.

In the version in which the shim 3 is present, the first ribs 10 of the upper surface 9 of the shim 3 are arranged at the third ribs 22 of the tibial element 2. The recesses formed thereby determine areas in which the bone cement remains, facilitating the adhesion of the tibial element 2 with the shim 3.

The first, second and third ribs, respectively 10, 12, 22, serve spacing purposes, i.e. they separate the tibial element 2 and/or the shim 3 from the tibial bone and, possibly, the tibial element 2 from the shim 3, determining an optimal minimum layer of the bone cement, under any clinical condition, so that there occurs the correct adhesion between the tibial element and/or the shim 3 and the tibial bone.

In a version of the invention, there is present at least one portion of shim 3 or more than one shim 3, depending on the specific conditions of the patient. In particular, when the tibial bone part is not parallel to the plane of the articulation, there can be inserted at least one portion of shim 3, so as to compensate the lacking bone area.

The femoral element 4 has a substantially "C-shaped" form comprising an inner concave surface 14, in contact with the bone seat, and an outer convex surface 15, adapted to enter in contact with the upper surface 16 of the tibial element 2. The femoral element 4, and in particular the inner surface 14 thereof, is adapted to be constrained to the free end of the femur using bone cement.

Figure 2:
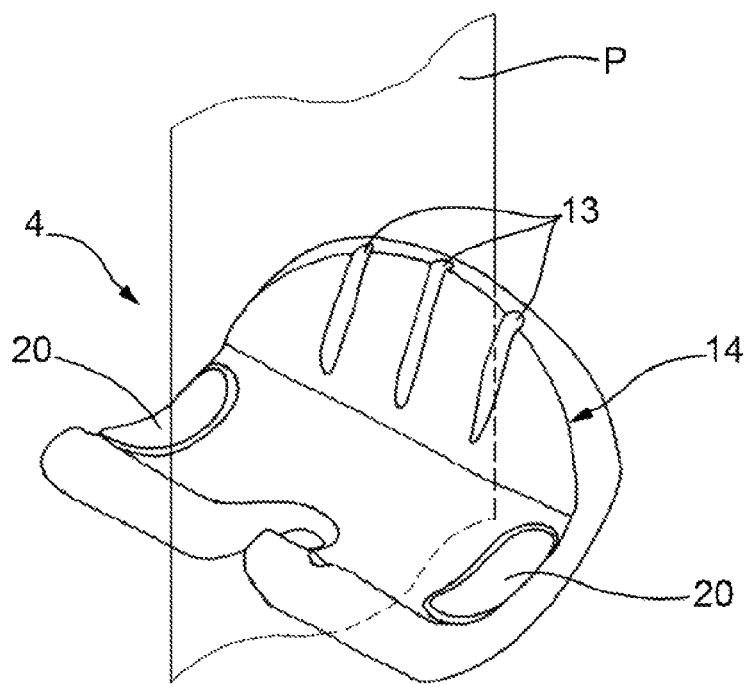
FIG. 2 is a perspective view of a detail of the device according to FIG. 1.
Figure 3:
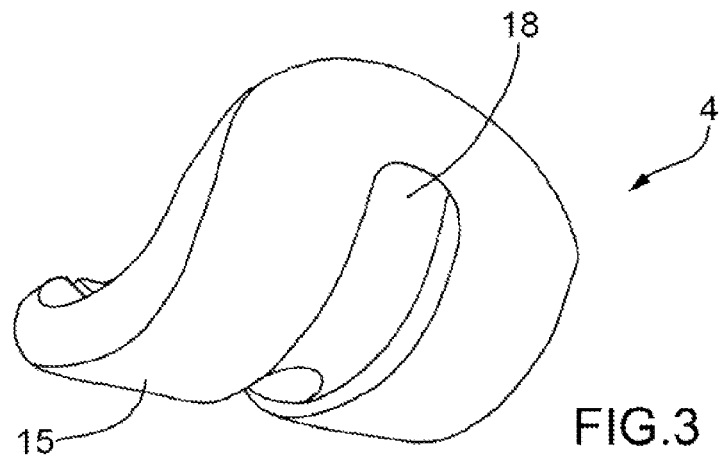
FIG. 3 is a perspective view of the detail of the device according to FIG. 2.

As indicated in the embodiment of FIG. 2, the femoral element 4, is provided with at least one groove 13 obtained in the inner surface 14 thereof. Such at least one groove 13 allows obtaining a better adhesion of the bone cement with the free end of the femur and with the femoral element 4.

In a particular embodiment of the femoral element 4, the inner surface 14 may comprise at least one projection 20. Such at least one projection 20 has a rounded shape and it is positioned in the lateral portions of the femoral element 4 (arranged at the lateral portions of the articulation of the knee).

Such at least one projection 20 allows obtaining an even more stable anchoring between the femoral element 4 and the femoral end itself.

Following the implantation of the modular spacer device 1, the outer surface 15 of the femoral element 4 is arranged in contact with the upper surface 16 of the tibial element 2.

The outer surface 15 of the femoral element 4 has a radius of curvature R1; the upper surface 16 of the tibial element 2 has a radius of curvature R2.

The radius of curvature R1 is smaller with respect to the radius of curvature R2.

In particular, the radius of curvature R2 is always greater than R1 and measures at least 1.5 R1. The radii of curvature R1 and R2 are selected so as to allow combining any femoral element 4 with any tibial element 2, as better described hereinafter. In order to obtain greater stability of the articulation formed by the modular spacer device 1, the tibial element 2 comprises a projecting element 17, abutting with a hollow seat 18 obtained on the outer surface 15 of the femoral element 4.

Figure 4:
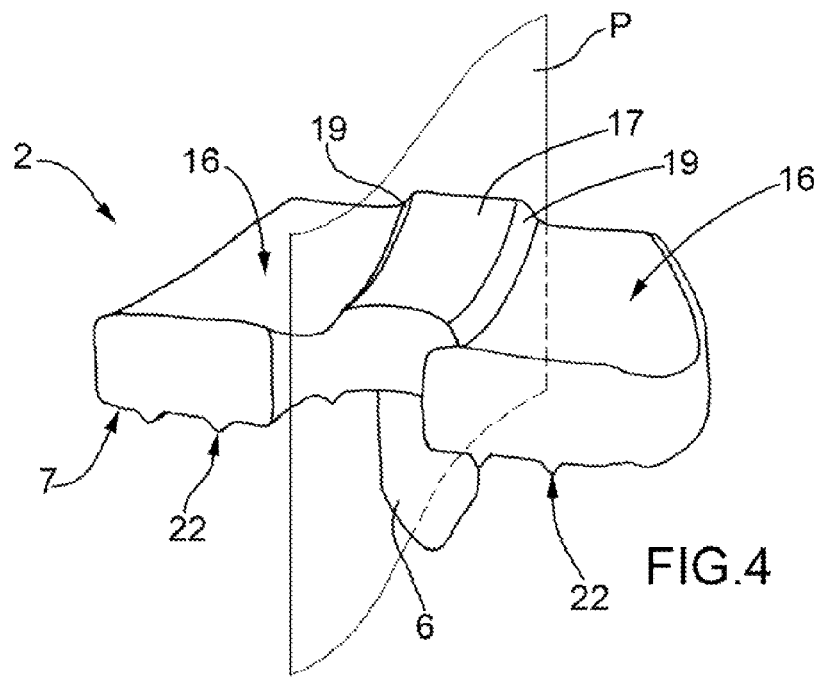
FIG. 4 is a perspective view of another detail of the device according to FIG. 1.

As indicated in FIG. 4, the projecting element 17 extends, longitudinally to the sagittal plane of the knee, i.e. to the rotation plane P, along the upper surface 16 and it is positioned centrally with respect to the tibial element 2. Correspondingly, the seat 18 extends, longitudinally to the sagittal plane of the knee, i.e. to the rotation plane P, along the outer surface 15 and it is positioned centrally with respect to the femoral element 4.

Such projecting element 17, similar to a notch, has rounded edges 19 so as to avoid damaging the femoral element 4 with which it comes to contact. In order to facilitate the modularity of the modular spacer device 1, the projecting element 17 and the seat 18 maintain the same dimensions, regardless of whether the dimensions of the tibial element 2 and of the femoral element 4 vary, as better described hereinafter.

Figure 6:
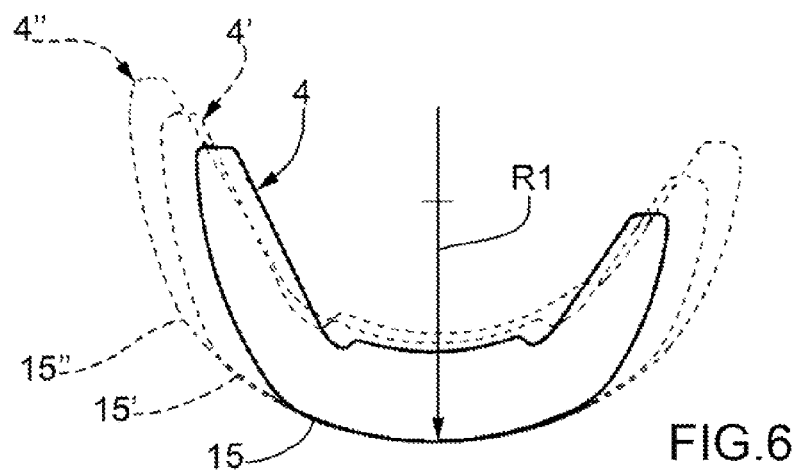
FIG. 6 is a lateral view of the various sizes of the detail according to FIG. 2.

Should the modular spacer device 1, during movement of the articulation of the knee, be subjected to lateral thrust stress, with respect to the rotation plane P of the articulation, the projecting element 17 maintains the femoral element 4 in the seat thereof, guaranteeing a correct movement and a good stability to the articulation. The femoral element 4, as indicated in FIG. 6, can be obtained in various dimensions or sizes, for example small, medium and large, as represented by the femoral element 4', 4", reproduced using a dashed line. The femoral element 4', 4" has an outer surface 15', 15" similar to the outer surface 15 of the femoral element 4.

Though the dimensions of the femoral element 4', 4" are greater with respect to the femoral element 4, the radius of curvature R1 of the outer surface 15, is equivalent to the radius of curvature R1 of the outer surface 15', 15".

Figure 7:
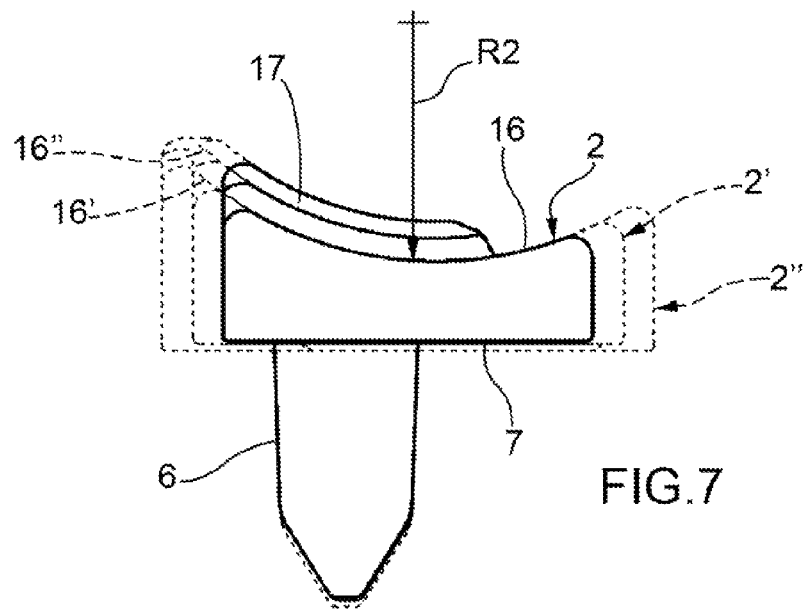
FIG. 7 is a lateral view of the various sizes of the detail according to FIG. 4.

Analogously, as indicated in FIGS. 7 and 8, there are provided further dimensions or sizes, for example small, medium and large, of the tibial element 2 and of the shim 3 represented by the tibial element 2', 2" and by the shim 3', 3", indicated with a dashed line. The tibial element 2', 2" has an upper surface 16', 16" similar to the upper surface 16 of the tibial element 2. In particular, the radius of curvature R2 of the upper surface 16 is equivalent to the radius of curvature R2 of the upper surface 16', 16".

Substantially, varying the sizes of the femoral element 4 and the tibial element 2, the radii R1 and R2 remain constant.

The various sizes of the tibial element 2, 2', 2" and of the femoral element 4, 4', 4" are interchangeable with respect to each other, due to the equivalence of the radius of curvature R1 between the outer surface 15, 15', 15" and due to the equivalence of the radius of curvature R2 of the upper surface 16, 16', 16".

Purely by way of non-limiting example, a possible embodiment of the modular spacer device 1 may provide for the use of a tibial element 2 and a femoral element 4". All possible combinations of the tibial element 2, 2', 2" and the femoral element 4, 4', 4" can be obtained though maintaining the correct stability and articulation with respect to each other.

Usually, regarding the dimensions of the shim 3, 3', 3", they correspond to those of the tibial element 2, 2', 2" used. For example, in case of use of a tibial element 2', the shim used will be 3', i.e. of the same size as the tibial element in question.

Such modularity of the spacer device 1 allows adapting the latter to the anthropomorphic dimensions of the femoral and tibial ends of a patient, which may differ with respect to each other.

The characteristics indicated above regarding the femoral element 4, the tibial element 2 and the shim 3 also refer to the femoral element 4', 4", the tibial element 2', 2" and the shim 3', 3".

The configuration of the radii of curvature R1 and R2 allows obtaining a mainly relative rolling motion between the femoral element 4, 4', 4" and the tibial element 2, 2', 2" and a partial sliding motion therebetween.

Such mainly rolling motion between the outer surface 15, 15', 15" of the femoral element 4, 4', 4" and the upper surface 16, 16', 16" of the tibial element 2, 2', 2" allows the patient to perform a flexion and extension motion of the articulation similar to the normal physiological motion of the articulation of the knee.

Adapting the modular spacer device 1 to the dimensions of each patient does not require any modification intervention of the tibial element 2, 2', 2" and of the femoral element 4, 4', 4", thus reducing the times required for the implantation of the modular spacer device 1. Actually, the surgeon is solely required to choose the best size of each element that forms the modular spacer device 1, in order to adapt each part to the actual dimensions of the respective anatomic seat of the patient, without necessarily requiring using a tibial element and a femoral element of the same size.

In order to guarantee the surgeon maximum freedom of choice, the femoral element 4, 4', 4", the tibial element 2, 2', 2" and the shim 3, 3', 3" will be packaged in separate packages and in one size.

The various configurations of the tibial element 2, 2', 2", of the shim 3, 3', 3" and of the femoral element 4, 4', 4", compatible to each other, guarantee the modular spacer device 1 a high modularity. In particular, the tibial element 2, 2', 2" is configured so as to be coupled with any size of the femoral element 4, 4', 4" to adapt the dimensions of the modular spacer device) with the dimensions of the bone ends to which it should be connected. This is obtained due to the fact that the radius R2 of the upper surface 16, 16', 16" of the tibial element 2, 2', 2" has a dimension such to be coupled rotatably and partly translatory with the radius R1, which is constant in the outer surface 15, 15', 15" of any size of the femoral element 4, 4', 4".

Therefore, the surgeon, instead of having a choice between three sizes, identical for the femoral and tibial parts, will have a wider choice, in particular nine possibilities, providing for obtaining three sizes (small, medium and large) for each femoral and tibial part separately. In addition, the possibilities increase in that it is possible to decide whether to use at least one portion of or at least one shim 3, 3', 3".

Furthermore, the configuration of the aforementioned modular spacer device 1 allows obtaining a high mobility of the articulation of the knee, and a movement similar to that of a natural articulation, though in presence of different anatomic dimensions, among the various articular portions of the patient.

The tibial 2 and femoral 4 elements, being pre-formed in various dimensions, simplify the stages of implantation thereof in the seat of the articulation, in that they do not require further forming operations or modifications of the dimensions thereof so as to be able to adapt them to the dimensions of the bone ends, actually reducing the times required for performing the surgical intervention and allowing, the patient, to have each part of the modular spacer device 1 perfectly suited to the actual bone and anatomic structure and/or compensate for possible faults due to pathologic and/or surgery conditions the patient is subjected to.

The possibility of pre-adding or adding the modular spacer device 1 using pharmacological and/or therapeutic products allows treating the local infections in the seat of the articulation and achieving the ideal conditions for implanting a new articular prosthesis.

The present invention thus conceived can be subjected to numerous modifications and variants all falling within the inventive concept.

Furthermore, all details can be replaced by other technically equivalent elements. In practice, the materials used, as well as contingent shapes and dimensions may vary depending on the requirements without departing from the scope of protection of the following claims.

The invention claimed is:

1. A disposable modular spacer device of the articulation of a knee comprising a tibial element, adapted to be constrained to an end of the tibial bone in proximity of the articulation of the knee, said tibial element comprising a lower surface and an upper surface provided with a radius of curvature R2, and a femoral element, said femoral element comprising an inner surface, adapted to be constrained to an end of the femoral bone at the articulation of the knee, and an outer convex surface, provided with a radius of curvature R1 and adapted to enter in contact with said upper surface of said tibial element, said tibial element and femoral element each being selected from tibial elements and femoral elements having various dimensions or sizes, wherein each size of said tibial element is interchangeable with each size of said femoral element to adapt the dimensions of said modular spacer device with the dimensions of the bone ends to which it should be connected.

2. The modular spacer device according to claim 1, comprising a shim, positioned beneath said tibial element.

3. The modular spacer device according to claim 2, wherein said shim has an upper surface and a lower surface, substantially flat, and/or a hole.

4. The modular spacer device according to claim 3, wherein said shim has, in said upper surface, first ribs and relative first recesses and/or wherein said tibial element has, in said lower surface, third ribs and corresponding third recesses, for holding said bone cement.

5. The modular spacer device according to claim 3, wherein said shim has, in said lower surface, second ribs and relative second recesses for the retention of said bone cement and for constraining said shim with the tibial bone of the patient.

6. The modular spacer device according to claim 2, wherein said tibial element, said femoral element and said shim are preformed and made of biologically compatible material.

7. The modular spacer device according to claim 6, wherein said biologically compatible material comprises at least one among the following materials: metals, metal alloys, organo-metallic compounds, ceramics, plastic materials, such as thermoplastic polymers, acrylic resins, polyethylene, polypropylene, polyesters, etcetera, thermoformable polymers, other similar materials, bone cement and/or a combination thereof.

8. The modular spacer device according to claim 6, wherein said biologically compatible material is porous.

9. The modular spacer device according to claim 8, wherein said porous biologically compatible material, originally without medicinal substances, is adapted to be impregnated using pharmaceutical and therapeutic products before the implantation of said device.

10. The modular spacer device according to claim 8, wherein said porous biologically compatible material is adapted to be pre-impregnated, by the producer of the modular spacer device, using pharmaceutical and therapeutic products.

11. The modular spacer device according to claim 10, wherein said porous biologically compatible material is adapted to be impregnated using pharmaceutical and therapeutic products before the implant of said device.

12. The modular spacer device according to claim 1, wherein said upper surface is concave and said lower surface is substantially flat.

13. The modular spacer device according to claim 1, wherein said radius of curvature R1 is smaller with respect to said radius of curvature R2.

14. The modular spacer device according to claim 1, wherein said radius of curvature R2 measures at least 1.5 R1.

15. The modular spacer device according to claim 1, wherein said tibial element comprises a substantially rod-like element which is extended from said lower surface downwards substantially in longitudinal direction with respect to the tibial bone of the patient and which is shaped similar to a pin or a stem or to a similar element, configured so as to be inserted into said hole.

16. The modular spacer device according to claim 1, wherein said tibial element is adapted to be constrained to the tibial bone of the patient using bone cement.

17. The modular spacer device according to claim 1, wherein said tibial element and said shim are adapted to be constrained to each other using bone cement and said shim is adapted to be constrained to the tibial bone of the patient using bone cement.

18. The modular spacer device according to claim 1, wherein said inner surface of said femoral element is provided with at least one groove and/or of at least one projection for a better adhesion of said inner surface with the femoral bone of a patient by using bone cement.

19. The modular spacer device according to claim 1, wherein said outer surface, of the radius R1, is in rotary and partly translatory contact with said upper concave surface of the radius R2.

20. The modular spacer device according to claim 1, wherein said outer convex surface comprises a hollow seat.

21. The modular spacer device according to claim 1, wherein said tibial element comprises a projecting element, abutting with said seat, for stabilising the movement of said modular spacer device.

22. The modular spacer device according to claim 21, wherein said projecting element extends, longitudinally to the sagittal plane of the knee, along said upper surface of said tibial element.

23. The modular spacer device according to claim 21, wherein said projecting element has rounded edges.

24. The modular spacer device according to claim 1, wherein the radius of curvature R2 of each of the tibial elements having various dimensions or sizes is constant, and the radius of curvature R1 of each of the femoral elements having various dimensions or sizes is constant.

25. A disposable modular spacer device of the articulation of a knee comprising:

a tibial element, adapted to be constrained to an end of the tibial bone in proximity of the articulation of the knee, said tibial element comprising a lower surface and an upper surface, said upper surface having a radius of curvature R2; and a femoral element, said femoral element comprising an inner surface adapted to be constrained to an end of the femoral bone at the articulation of the knee, and an outer convex surface provided with a radius of curvature R1 and adapted to enter in contact with said upper surface of said tibial element having the radius of curvature R2, wherein said tibial element is selected from a plurality of tibial elements having various dimensions or sizes and said femoral element is selected from a plurality of femoral elements having various dimensions or sizes, wherein the radius of curvature R2 of each of the tibial elements having various dimensions or sizes is constant, and the radius of curvature R1 of each of the femoral elements having various dimensions or sizes is constant.

* * * * *